(12) United States Patent
Gofman

(10) Patent No.: US 11,910,531 B2
(45) Date of Patent: Feb. 20, 2024

(54) FLEXIBLE PRINTED CIRCUIT BOARD HAVING A BATTERY MOUNTED THERETO

(71) Applicant: Ascensia Diabetes Care Holdings AG, Basel (CH)

(72) Inventor: Igor Y. Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 500 days.

(21) Appl. No.: 17/199,408

(22) Filed: Mar. 11, 2021

(65) Prior Publication Data
US 2021/0289631 A1   Sep. 16, 2021

Related U.S. Application Data

(60) Provisional application No. 62/989,587, filed on Mar. 13, 2020.

(51) Int. Cl.
*H05K 1/18* (2006.01)
*A61B 5/00* (2006.01)
(Continued)

(52) U.S. Cl.
CPC .......... *H05K 1/189* (2013.01); *A61B 5/0002* (2013.01); *A61B 5/14532* (2013.01);
(Continued)

(58) Field of Classification Search
CPC ........ H05K 1/189; H05K 1/113; H05K 1/118; H05K 1/181; H05K 3/284; H05K 3/287;
(Continued)

(56) References Cited

U.S. PATENT DOCUMENTS

| 2014/0266939 A1* | 9/2014 | Baringer | ............ | A61B 5/02427 |
| | | | | 343/729 |
| 2019/0036289 A1 | 1/2019 | Hirasawa et al. | | |
| 2021/0289631 A1 | 9/2021 | Gofman | | |

FOREIGN PATENT DOCUMENTS

| CN | 115428597 A | 12/2022 |
| EP | 1030366 A2 | 8/2000 |
| | (Continued) | |

OTHER PUBLICATIONS

International Search Report of International Application No. PCT/EP2021/056320 dated Jun. 29, 2021.
(Continued)

*Primary Examiner* — Binh B Tran
(74) *Attorney, Agent, or Firm* — Erise IP, P.A.

(57) ABSTRACT

A flexible printed circuit board (PCB) may have one or more coin cell batteries mounted thereto such that the flexibility of the flexible PCB is maintained. The flexible PCB has one or more battery contact pads fabricated thereon. Each battery contact pad includes a pattern of metalized vias each extending from a top surface to a bottom surface of the flexible PCB. A coin cell battery may be positioned over or under the battery contact pad. Conductive light curable epoxy is applied to and in each metalized via to contact and adhere to the coin cell battery to form a conductive path from the battery through the battery contact pad to printed conductors on the flexible PCB. Methods of mounting one or more coin cell batteries to a flexible PCB are also provided, as are other aspects.

20 Claims, 9 Drawing Sheets

(51) Int. Cl.
- *A61B 5/145* (2006.01)
- *H05K 1/11* (2006.01)
- *H05K 3/28* (2006.01)

(52) U.S. Cl.
CPC .............. *H05K 1/113* (2013.01); *H05K 1/118* (2013.01); *H05K 1/181* (2013.01); *H05K 3/284* (2013.01); *H05K 3/287* (2013.01); *H05K 2201/10037* (2013.01); *H05K 2201/10098* (2013.01); *H05K 2201/10151* (2013.01); *H05K 2203/1377* (2013.01)

(58) Field of Classification Search
CPC .......... H05K 2201/10037; H05K 2201/10098; H05K 2201/10151; H05K 2201/1377; A61B 5/0002; A61B 5/14532
USPC ........................................................ 361/748
See application file for complete search history.

(56) References Cited

FOREIGN PATENT DOCUMENTS

| | | |
|---|---|---|
| EP | 3588616 A1 | 1/2020 |
| EP | 4118940 A1 | 1/2023 |
| WO | WO2012144493 A1 | 10/2012 |
| WO | WO2013106056 A2 | 7/2013 |
| WO | 2021180917 A1 | 9/2021 |

OTHER PUBLICATIONS

Chinese Patent Office, Notification of Publication, Application No. 12134222526783, dated Dec. 8, 2022.

Canadian Patent Application 3,171,398 Examination Report dated Nov. 7, 2023.

* cited by examiner

FLEXIBLE PRINTED CIRCUIT BOARD HAVING A BATTERY MOUNTED THERETO

CROSS REFERENCE TO RELATED APPLICATION

This claims the benefit of U.S. Provisional Patent Application No. 62/989,587, filed Mar. 13, 2020, the disclosure of which is hereby incorporated herein by reference in its entirety for all purposes.

FIELD

The present invention relates generally to battery-operated devices and, more particularly, to a battery-operated device having a flexible printed circuit board (PCB).

BACKGROUND

A flexible PCB is an assembly of electronic circuits and components fabricated on a flexible substrate. Compared to rigid PCBs, flexible PCBs have numerous advantages including a capability of conforming to a desired shape (e.g., curved). Many small battery-operated electronic devices may benefit from having a flexible PCB. However, the one or more batteries and battery holders of such devices are typically the thickest part of an electronic assembly on a PCB and thus would add rigidity to the PCB, defeating the purpose of having a flexible PCB. Accordingly, a need exists to provide battery power to small battery-operated electronic devices having a flexible PCB without adversely affecting the flexibility of the flexible PCB.

SUMMARY

According to one aspect, a flexible printed circuit board (PCB) is provided that includes the following: a metalized via extending through the flexible PCB from a first surface to an opposite second surface of the flexible PCB, a battery in contact with the first surface and covering the metalized via, and a conductive light curable epoxy disposed on the second surface over and in the metalized via such that the conductive light curable epoxy contacts and adheres to the battery and provides a conductive path from the battery to the metalized via.

According to another aspect, a flexible PCB is provided that includes first and second sections, wherein the first section is separated from the second section by a slit extending through the flexible PCB from a top surface to a bottom surface. The flexible PCB also includes first and second metalized vias, wherein the first metalized via extends through the flexible PCB from the top surface to the bottom surface in the first section, and the second metalized via extends through the flexible PCB from the top surface to the bottom surface in the second section. The flexible PCB further includes a battery inserted in the slit such that the battery contacts the bottom surface of the first section under the first metalized via and contacts the top surface of the second section over the second metalized via. The flexible PCB still further includes a first conductive light curable epoxy and a second conductive light curable epoxy. The first conductive light curable epoxy is disposed on the top surface of the first section over and in the first metalized via such that the first conductive light curable epoxy contacts and adheres to the battery and provides a conductive path from the battery to the first metalized via. And the second conductive light curable epoxy is disposed on the bottom surface of the second section over and in the second metalized via such that the second conductive light curable epoxy contacts and adheres to the battery and provides a conductive path from the battery to the second metalized via.

According to a further aspect, a flexible PCB is provided that includes the following: a first metalized via extending through the flexible PCB from a top surface to a bottom surface of the flexible PCB, a battery positioned on the top surface over the first metalized via, a first conductive light curable epoxy disposed on the bottom surface of the flexible PCB over and in the first metalized via such that the first conductive light curable epoxy contacts and adheres to the battery and provides a conductive path from the battery to the first metalized via, an arm having a second metalized via extending through the arm from a top surface to a bottom surface of the arm, the arm positioned on the battery such that the bottom surface of the arm contacts the battery and the second metalized via is over the battery, and a second conductive light curable epoxy disposed on the top surface of the arm over and in the second metalized via such that the second conductive light curable epoxy contacts and adheres to the battery and provides a conductive path from the battery to the second metalized via.

Still other aspects, features, and advantages of this disclosure may be readily apparent from the following detailed description and illustration of a number of example embodiments and implementations, including the best mode contemplated for carrying out the invention. This disclosure may also be capable of other and different embodiments, and its several details may be modified in various respects, all without departing from the scope of the invention. This disclosure is intended to cover all modifications, equivalents, and alternatives falling within the scope of the appended claims (see further below).

BRIEF DESCRIPTION OF DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

A flexible printed circuit board (PCB) may include an assembly of electronic circuits and/or components surface mounted on a flexible plastic substrate, for example. The flexible plastic substrate may be, e.g., a polyimide, polyether ether ketone (PEEK), a conductive transparent polyester film or the like. Flexible PCBs are typically very thin, usually no more than a few millimeters thick. A flexible PCB can advantageously bend or flex during its use. In contrast, rigid PCBs, which are thicker than flexible PCBs, may break and/or the circuitry imprinted thereon may malfunction if they are bent or flexed during use.

A small battery-operated electronic device that may benefit from having a flexible PCB is a continuous glucose monitor (CGM) wireless transmitter. A CGM wireless transmitter may be placed on a user's body to automatically take glucose measurements at regular intervals and wirelessly transmit those measurements to a receiver and/or an insulin pump. A CGM wireless transmitter with a flexible PCB for a sensor and wireless transmitter circuitry may allow the CGM wireless transmitter to conform to the surface of a user's body at the attachment site, thus improving the CGM wireless transmitter's adhesion thereto and/or the user's comfort while wearing the CGM wireless transmitter. CGMs are typically powered by coin cell batteries, such as, e.g., miniature silver oxide batteries. However, coin cell batteries held in conventional coin cell battery holders, which are generally configured for mounting to rigid PCBs, would defeat the purpose of having a flexible PCB because the thickness and size of the battery holders would add rigidity to the flexible PCB.

In accordance with the embodiments disclosed herein, coin cell batteries (and batteries with a similar configuration) may be mounted directly to a flexible PCB without using conventional battery holders. Such direct mounting maintains the overall flexibility of a flexible PCB by minimizing the additional thickness added to the flexible PCB by the coin cell batteries. For example, in one embodiment, a flexible PCB having a one or more coin cell batteries mounted directly thereon may have a maximum thickness of only about 1.6 mm, thus allowing a CGM wireless transmitter with a flexible PCB to readily conform to the surface of a user's body at the attachment site.

To ensure a reliable mechanical and electrical connection between a battery and a flexible PCB, a battery contact pad formed on the flexible PCB and methods of connecting batteries to a flexible PCB in accordance with one or more embodiments are provided, as will be explained in greater detail below in connection with FIGS. 1A-12.

Figure 1A:
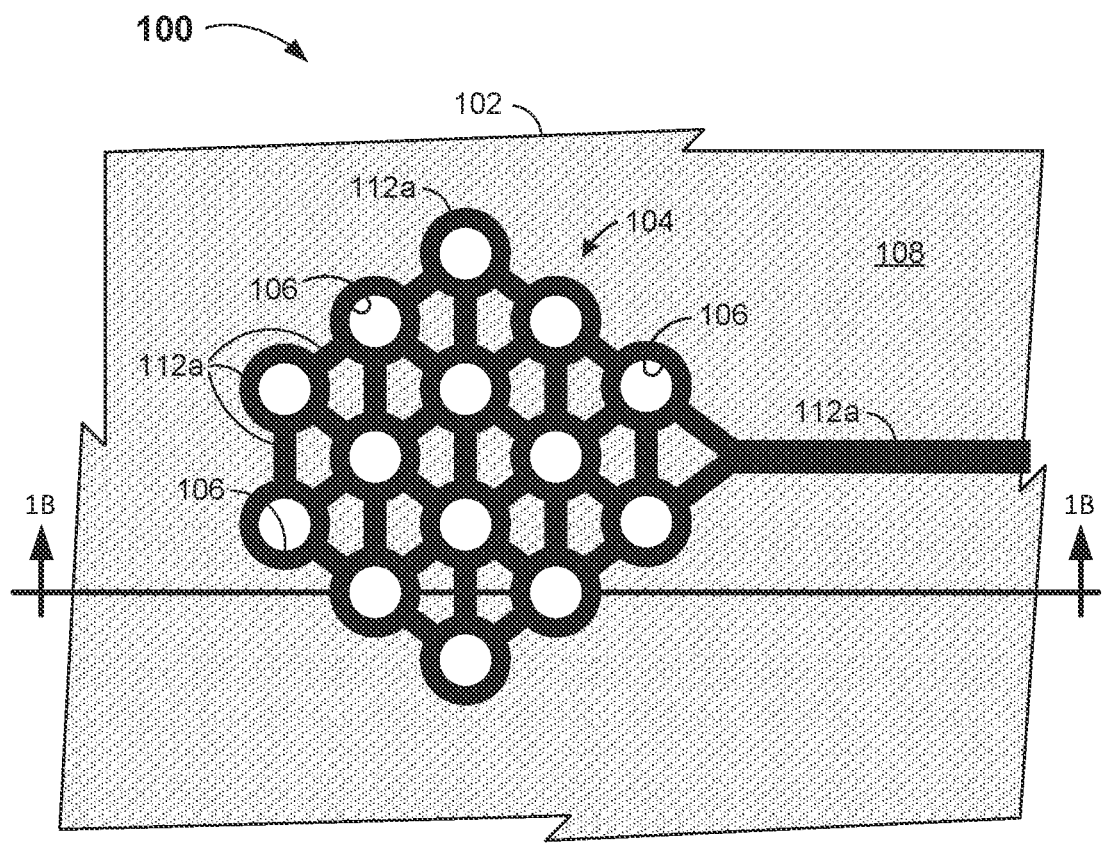
FIG. 1A illustrates a plan view of a portion of a flexible printed circuit board (PCB) having a battery contact pad formed thereon according to embodiments.
Figure 1B:
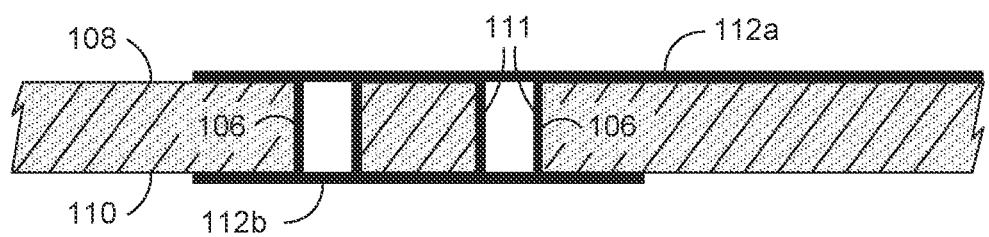
FIG. 1B illustrates a cross-sectional side view of the portion of the flexible PCB of FIG. 1A taken along section line 1B-1B of FIG. 1A.

FIGS. 1A and 1B illustrate a portion 100 of a flexible PCB 102 having a battery contact pad 104 formed thereon in accordance with one or more embodiments. Battery contact pad 104 includes a plurality of metalized vias 106 (only a few labeled in FIG. 1A) arranged in a pattern. Other suitable patterns than the one shown may be used. Each metalized via 106 is a through hole that extends through flexible PCB 102 from a first surface 108 to an opposite second surface 110 of flexible PCB 102. A conductive metal 111, such as, e.g., copper, may be disposed on and over the inside surface of each metalized via 106. Other suitable conductive metals may be used. A printed conductor 112a formed on first surface 108 surrounds and electrically connects the plurality of metalized vias 106 to each other, and a printed conductor 112b formed on second surface 110 also surrounds and electrically connects the plurality of metalized vias 106 to each other. Accordingly, the plurality of metalized vias 106 electrically connects printed conductors 112a and 112b to each other. Printed conductors 112a and 112b may be copper or any other electrical conductor suitable for printing on a flexible PCB. In some embodiments, each metalized via 106 may have a diameter ranging from 0.5 mm to 2 mm, and battery contact pad 104 may have a diameter ranging from 3 mm to 15 mm.

Figure 2:
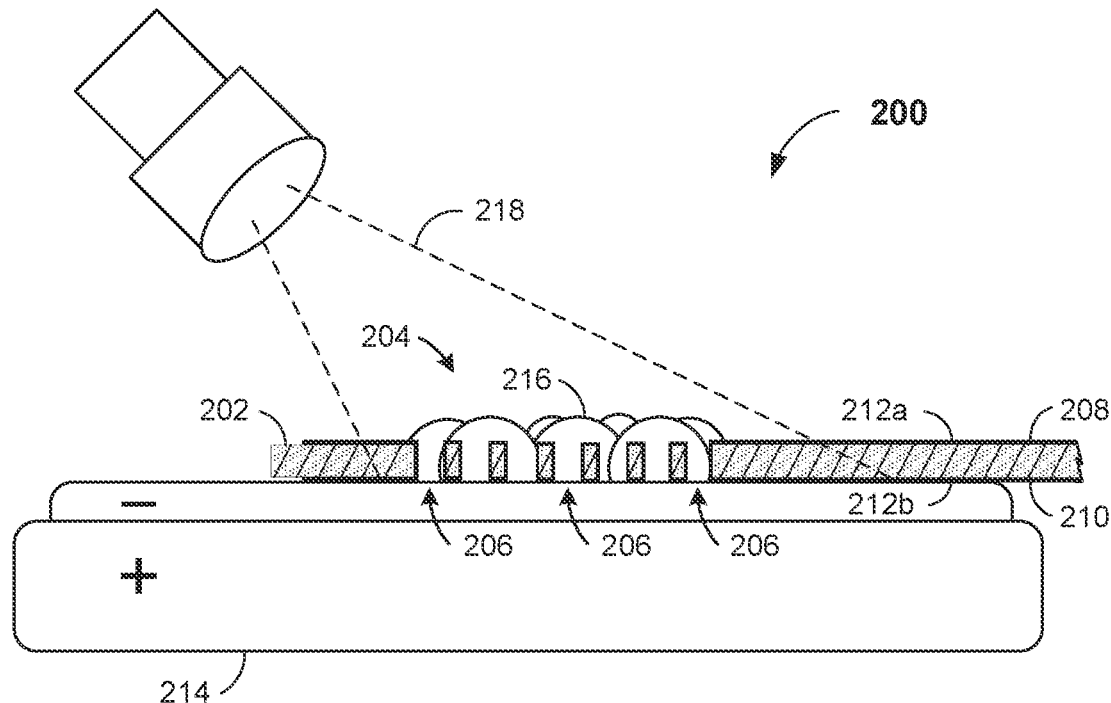
FIG. 2 illustrates a cross-sectional side view of another portion of a flexible PCB having a coin cell battery mounted and electrically connected thereto according to embodiments.

FIG. 2 illustrates a portion 200 of a flexible PCB 202 having a battery 214 attached to a battery contact pad 204 on a bottom surface 210 of flexible PCB 202 in accordance with one or more embodiments. Battery contact pad 204 may be similar or identical to battery contact pad 104. Battery 214 may be a coin cell battery and, more particularly, may be a miniature silver oxide battery. Alternatively, battery 214 may be of another type having a similar configuration (e.g., having a flat surface). A conductive light curable epoxy, such as conductive ultraviolet curable epoxy 216, is disposed on top surface 208 over and in each metalized via 206 (only three labeled in FIG. 2) such that conductive ultraviolet curable epoxy 216 contacts and adheres to battery 214 and provides a conductive path from battery 214 through the metalized vias 206 to printed conductor 212a (and, in some embodiments, to a printed conductor 212b on bottom surface 210). Printed conductor 212a may be connected to other circuitry, components, or connectors (not shown) on flexible PCB 202. Conductive ultraviolet curable epoxy 216 may be, e.g., Elecolit® 3063, 3064, or 3065 by Panacol-Elosol GmbH. Advantageously, battery 214 is mounted directly to flexible PCB 202 without a battery holder.

Figure 3:
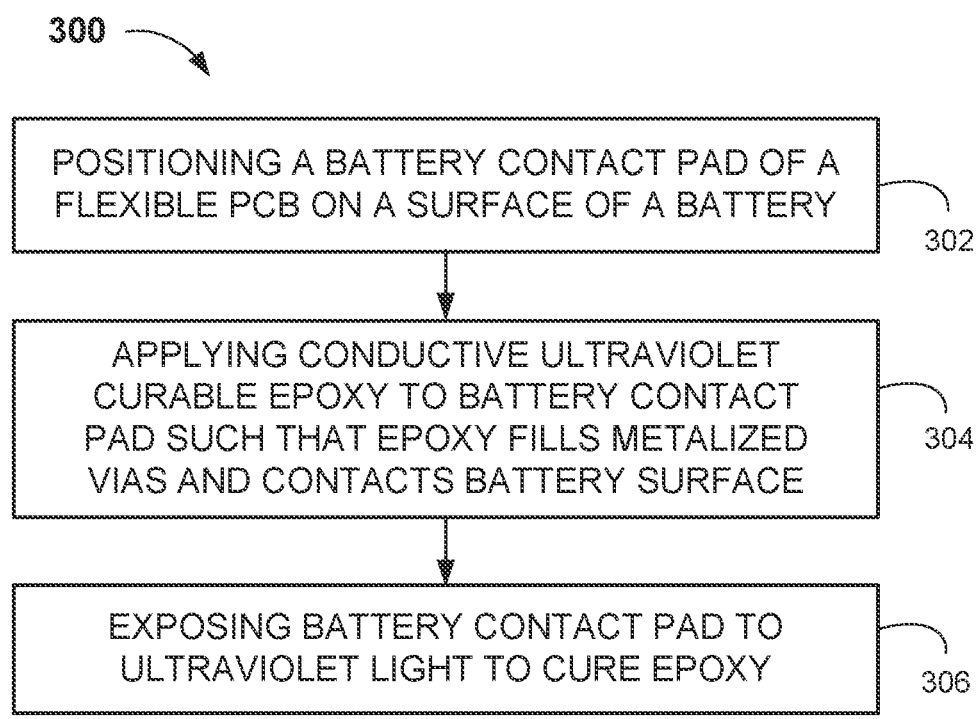
FIG. 3 illustrates a flowchart of a method of mounting a coin cell battery to a flexible PCB according to embodiments.

FIG. 3 illustrates a method 300 of mounting a battery to a flexible PCB in accordance with one or more embodiments. At process block 302, method 300 can include positioning a battery contact pad of a flexible PCB on a surface of a battery. As shown in FIG. 2, e.g., battery contact pad 204 of flexible PCB 202 may be positioned on a top surface of coin cell battery 214.

At process block 304, method 300 can include applying conductive ultraviolet curable epoxy to the battery contact pad such that the conductive ultraviolet curable epoxy fills the metalized vias of the battery contact pad and contacts the surface of the battery. The conductive ultraviolet curable epoxy is used as an adhesive and/or a "cold" solder for surface mounting components, particularly heat sensitive components, to a flexible PCB. The conductive ultraviolet curable epoxy may be applied in any suitable manner and should at least substantially fill enough of the metalized vias such that a sufficient amount contacts the surface of battery to establish a reliable mechanical and electrical connection between the battery and metalized vias. Referring again to FIG. 2, conductive ultraviolet curable epoxy 216 preferably completely fills each of metalized vias 206 and fully contacts the top surface of battery 214.

At process block 306, method 300 can include exposing the battery contact pad to ultraviolet light to cure the conductive ultraviolet curable epoxy. As shown in FIG. 2, conductive ultraviolet curable epoxy 216 covering battery contact pad 204 may be exposed to ultraviolet light 218 to cure conductive ultraviolet curable epoxy 216, thus establishing a reliable mechanical and electrical connection between battery 214 and metalized vias 206. Depending on the power of the ultraviolet light, epoxy type, and ambient temperature, curing time may range from a few seconds to a minute or so. Once cured, a robust conductive junction is formed between the battery and the battery contact pad.

Notably, the pattern of metalized vias on the battery contact pad advantageously facilitates the curing of the conductive ultraviolet curable epoxy such that little to no epoxy remains uncured. Uncured epoxy may weaken or even prevent a reliable mechanical and electrical connection from forming. The pattern of metalized vias increases the conductive area, which lowers the total connection resistance, and the relatively large vias allow the ultraviolet light to reach the bottom of the epoxy in each via (i.e., at the battery surface), which improves curing.

To complete the electrical connection to battery 214 shown in FIG. 2 (wherein only one terminal, e.g., the negative terminal, is shown connected), a second connection needs to be made to the other terminal (e.g., the positive terminal) on the bottom surface of battery 214. FIGS. 4A, 4B, 6A-6C, and 8 illustrate several embodiments in which the second connection to the battery can be made while advantageously maintaining the overall flexibility of the flexible PCB.

Figure 4A:
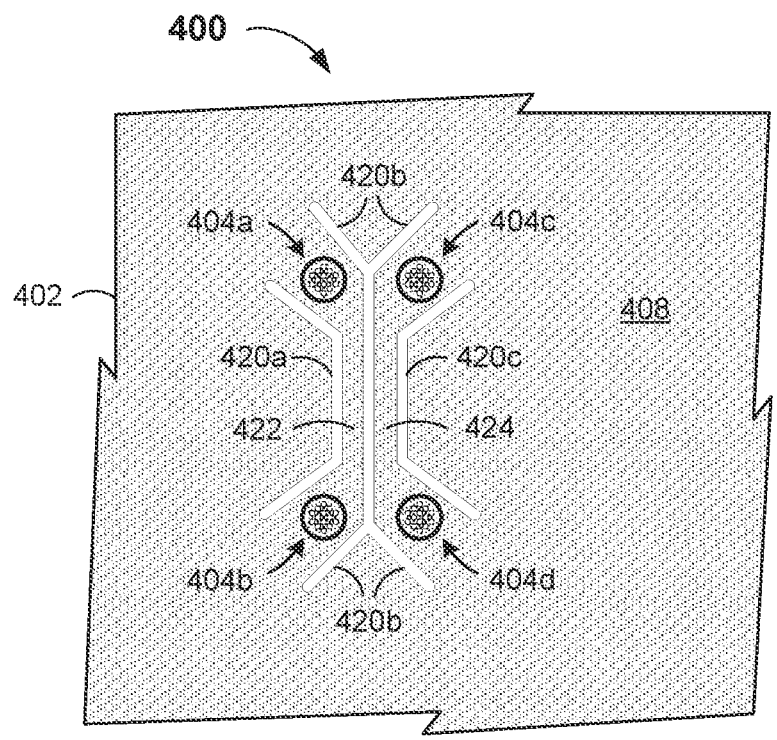
FIGS. 4A and 4B illustrate a plan view of another portion of a flexible PCB having a plurality of slits or cuts arranged there through to accommodate mounting and electrical connection of one or more batteries to the flexible PCB according to embodiments.
Figure 4B:
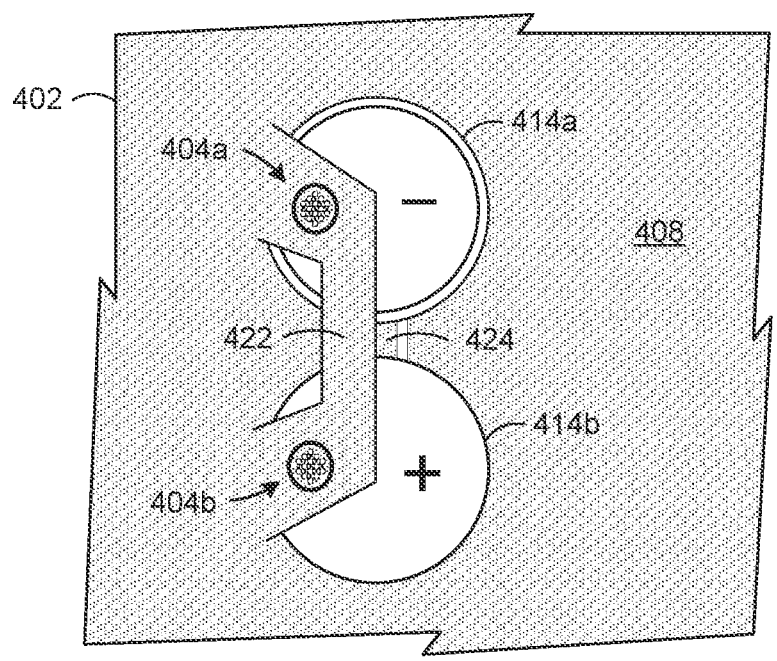

FIGS. 4A and 4B illustrate a portion 400 of a flexible PCB 402 having battery contact pads 404a-404d and a plurality of slits or cuts 420a, 420b, and 420c arranged in flexible PCB 402 to accommodate the mounting of one or more coin cell batteries 414a and 414b (or batteries with similar configuration) to flexible PCB 402 at battery contact pads 404a-404d in accordance with one or more embodiments. Each of battery contact pads 404a-404d may be similar or identical to battery contact pad 104. Slits 420a-420c each extend through flexible PCB 402 from a top surface 408 to a bottom surface (not shown in FIGS. 4A and 4B) of flexible PCB 402. Slits 420a-420c may be made in any suitable manner. Slits 420a and 420b form a first section 422 that includes battery contact pads 404a and 404b, and slits 420b and 420c form a second section 424 that includes battery contact pads 404c and 404d. First section 422 is separated from second section 424 by slit 420b.

As shown in FIG. 4B, battery 414a may be inserted in slit 420b and through slit 420a such that one surface of battery 414a (e.g., the negative terminal surface as shown) contacts the bottom surface of first section 422 under battery contact pad 404a (and its metalized vias) and the opposite surface (e.g., the positive terminal surface) contacts the top surface 408 of second section 424 over battery contact pad 404c (and its metalized vias). Similarly, battery 414b may be inserted in slit 420b and through slit 420a such that one surface of battery 414a (e.g., the positive terminal surface as shown) contacts the bottom surface of first section 422 under battery contact pad 404a (and its metalized vias) and the opposite surface (e.g., the negative terminal surface) contacts the top surface 408 of second section 424 over battery contact pad 404c (and its metalized vias).

Figure 5:
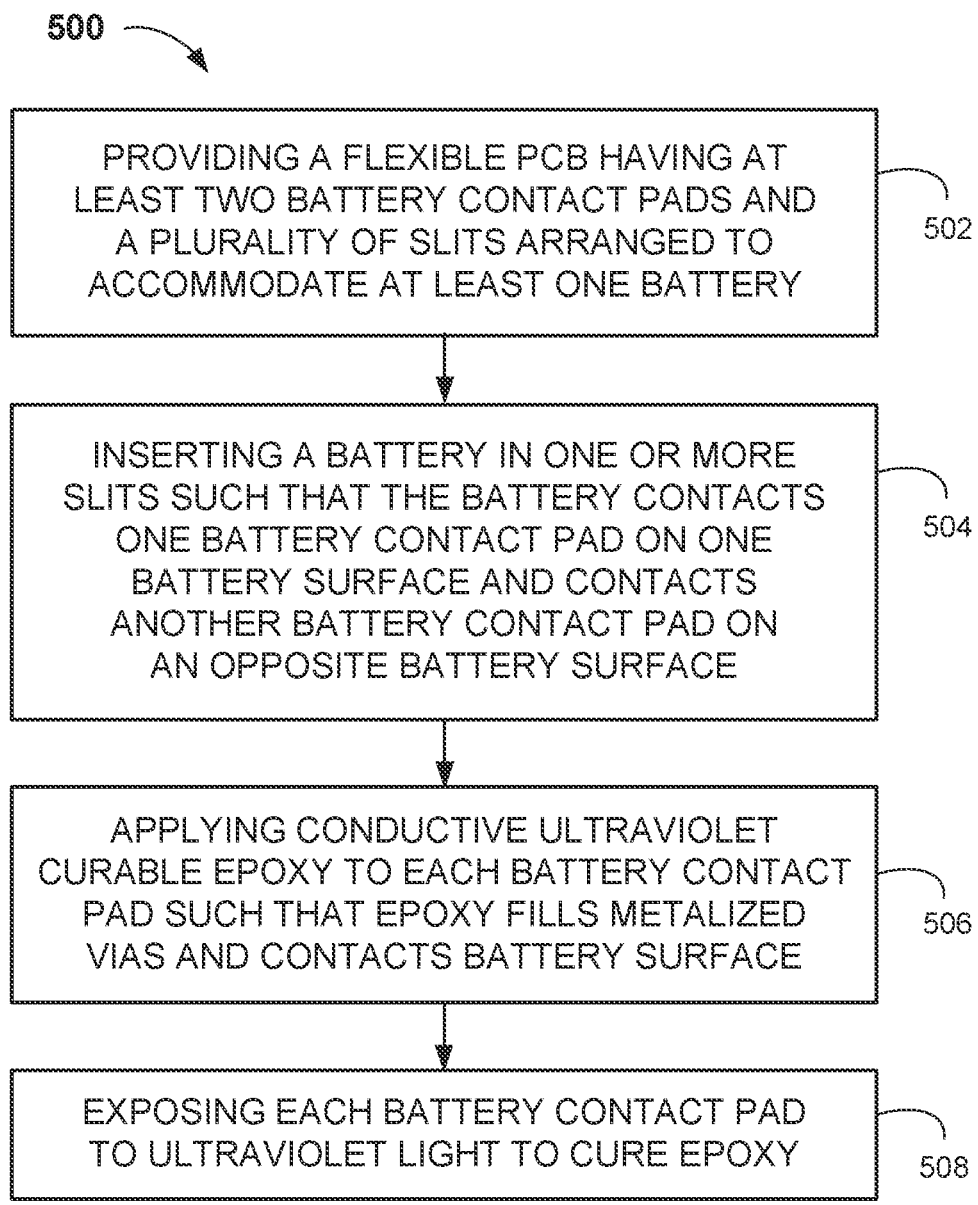
FIG. 5 illustrates a flowchart of another method of mounting a coin cell battery to a flexible PCB according to embodiments.

To form mechanical and electrical connections between batteries 414a and 414b and battery contact pads 404a-404d, conductive ultraviolet curable epoxy may be disposed over and in each plurality of metalized vias of battery contact pads 404a-404d such that the conductive ultraviolet curable epoxy contacts and, after curing by ultraviolet light, adheres to each battery 414a and 414b and provides a conductive path from each battery 414a and 414b to its respective pair of battery contact pad 404a-404d (and plurality of metalized vias), as similarly shown, e.g., in FIG. 2, and as described below in connection with FIG. 5.

Note that in some embodiments, depending on the configuration of imprinted and/or mounted circuitry and/or components (not shown) on flexible PCB 402, batteries 414a and 414b may instead be inserted under second section 424 to contact battery contact pads 404a-404d in an opposite manner as that shown in FIG. 4B.

Note also that printed conductors (not shown) may electrically connect battery contact pads 404a-404d to other circuitry and/or components imprinted and/or mounted on flexible PCB 402.

Note further that although two batteries 414a and 414b are shown, in other embodiments portion 400 and slits 420a-420c may be configured to accommodate just a single coin cell battery, depending on the power needs of the circuitry and/or components imprinted and/or mounted on flexible PCB 402.

FIG. 5 illustrates a method 500 of mounting a coin cell battery (or battery with a similar configuration) to a flexible PCB having a plurality of slits for accommodating the battery in accordance with one or more embodiments. At process block 502, method 500 can include providing a flexible PCB having at least two battery contact pads and a plurality of slits arranged to accommodate at least one battery. For example, as shown in FIG. 4A, flexible PCB 402 may be provided with battery contact pads 404a-404d and a plurality of slits 420a, 420b, and 420c arranged to accommodate one or more coin cell batteries 414a and/or 414b.

At process block 504, method 500 can include inserting a battery in one or more slits such that the battery contacts one battery contact pad on one surface of the battery and contacts another battery contact pad on an opposite surface of the battery. For example, as shown in FIG. 4B, battery 414a may be inserted in slit 420b and through slit 420a such that one surface of battery 414a (e.g., the negative terminal surface as shown) contacts battery contact pad 404a (and its metalized vias) and the opposite surface (e.g., the positive terminal surface) of battery 414a contacts battery contact pad 404c (and its metalized vias).

At process block 506, method 500 can include applying conductive ultraviolet curable epoxy to the accessible side of each contact pad such that the epoxy fills the metalized vias of each contact pad and contacts the battery surface. For example, referring to FIGS. 2, 4A, and 4B, a first conductive ultraviolet curable epoxy (such as, e.g., conductive ultraviolet curable epoxy 216) may be applied on top surface 408 of first section 422 over and in battery contact pad 404a (and its metalized vias) such that the first conductive ultraviolet curable epoxy contacts the negative terminal surface of battery 414a. Furthermore, a second conductive ultraviolet curable epoxy (such as, e.g., conductive ultraviolet curable epoxy 216) may be applied on a bottom surface of second section 424 (not shown in FIG. 4B) over and in battery contact pad 404c (and its metalized vias) such that the second conductive ultraviolet curable epoxy contacts the positive terminal surface of battery 414a (not shown in FIG. 4B).

At process block 508, method 500 can include exposing each battery contact pad to ultraviolet light to cure the conductive ultraviolet curable epoxy. Referring to FIG. 4B and continuing with the above example, the first conductive ultraviolet curable epoxy over and in battery contact pad 404a may be exposed to ultraviolet light (such as, e.g., ultraviolet light 218 of FIG. 2) to cure the first conductive ultraviolet curable epoxy, thus establishing a reliable mechanical connection between the negative terminal surface of battery 414a and battery contact pad 404a (i.e., the cured epoxy adheres to the battery surface and metalized vias). A conductive path from the negative terminal surface of battery 414a to and through battery contact pad 404a (by way of its metalized vias) is also established. Similarly, the second conductive ultraviolet curable epoxy over and in battery contact pad 404c may be exposed to ultraviolet light (such as, e.g., ultraviolet light 218 of FIG. 2) to cure the second conductive ultraviolet curable epoxy, thus establishing a reliable mechanical connection between the positive terminal surface of battery 414a and battery contact pad 404c. A conductive path from the positive terminal surface of battery 414a to and through battery contact pad 404c (by way of its metalized vias) is also established. Note that the first and second conductive ultraviolet curable epoxies may be exposed to ultraviolet light sequentially or concurrently (e.g., by one ultraviolet lighting device directed at top surface 408 and another ultraviolet lighting device directed at the bottom surface (not shown) of flexible PCB 402).

Figure 6A:
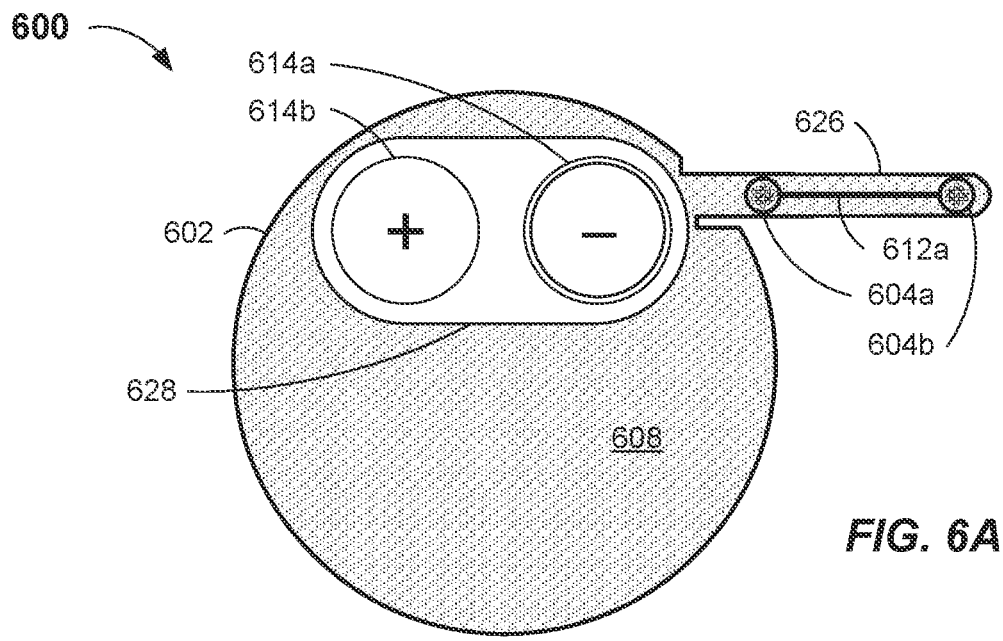
FIG. 6A illustrates a plan view of a flexible PCB having a foldable arm extending therefrom according to embodiments.
Figure 6B:
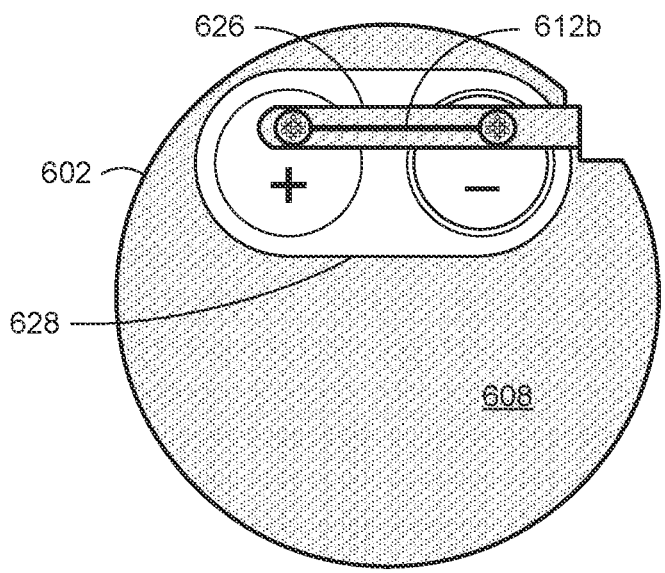
FIGS. 6B and 6C illustrate plan and side views, respectively, of the flexible PCB of FIG. 6A with the foldable arm folded to mount and electrically connect a pair of coin cell batteries to the flexible PCB according to embodiments.
Figure 6C:
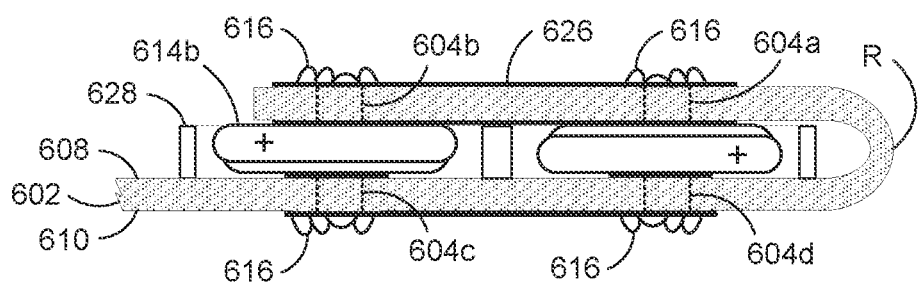

FIGS. 6A-6C illustrate a flexible PCB configuration 600 having a foldable arm 626 configured to mount and electrically connect a pair of coin cell batteries 614a and 614b (or batteries with a similar configuration) to a flexible PCB 602 in accordance with one or more embodiments. As shown in FIG. 6A, flexible PCB 602 initially has folding arm 626 extending therefrom. Foldable arm 626 may have battery contact pads 604a and 604b formed therein that may be connected to each other by a printed conductor 612a on one surface of foldable arm 626 and, in some embodiments, by a printed conductor 612b on the opposite surface of foldable arm 626 (see FIG. 6B). Each of battery contact pads 604a and 604b may be similar or identical to battery contact pad 104. Flexible PCB 602 may have one or more coin cell batteries 614a and 614b placed on a top surface 608 of flexible PCB 602 over respective battery contact pads 604c and 604d (see FIG. 6C) formed in flexible PCB 602. Each of battery contact pads 604c and 604d may also be similar or identical to battery contact pad 104. In those embodiments where only a single battery is required, foldable arm 626 and flexible PCB 602 may each have just one appropriately positioned battery contact pad, and the length of foldable arm 626 may be adjusted accordingly.

In those embodiments where some rigidity to the area where the battery or batteries are to be mounted is desired to facilitate an assembly process of flexible PCB 602, a non-conductive battery stiffener 628 may be used to hold batteries 614a and 614b. Battery stiffener 628 may have a height or thickness no greater than the height or thickness of batteries 614a and 614b. Any suitable non-conductive material (e.g., a rigid plastic) may be used to make battery stiffener 628. Battery stiffener 628 may advantageously provide rigidity to the battery mounting area without increasing the height of the PCB assembly of batteries, circuits, and/or components. The flexibility of the remaining portion of flexible PCB 602 is not adversely affected by battery stiffener 628.

FIGS. 6B and 6C illustrate flexible PCB 602 having foldable arm 626 folded over and onto batteries 614a and 614b. In some embodiments, the radius R at the fold of foldable arm 626 may be about 1.5 mm (+/−0.1 mm). Foldable arm 626 is configured to fold over onto only one surface of flexible PCB 602 (e.g., onto top surface 608 as shown). That is, foldable arm 626 is fabricated with a pre-cut to fold onto either the top or bottom surface of flexible PCB 602, but not both. Foldable arm 626 may be mechanically and electrically connected to batteries 614a and 614b by application and curing of conductive ultraviolet curable epoxy 616 disposed over and in each of battery contact pads 604a and 604b from the top surface of foldable arm 626 (as shown in FIG. 6C) in a same or similar manner as described above in connection with FIGS. 2, 3, 4B, and 5. Likewise, batteries 614a and 614b may be mechanically and electrically connected to top surface 608 of flexible PCB 602 by application and curing of conductive ultraviolet curable epoxy 616 disposed over and in each of battery contact pads 604c and 604d from a bottom surface 610 of flexible PCB 602 in a same or similar manner as described above in connection with FIGS. 2, 3, 4B, and 5. Note that the curing of conductive ultraviolet curable epoxies 616 in and over battery contact pads 604a-604d by ultraviolet light may be performed concurrently or in any suitable order.

Figure 7:
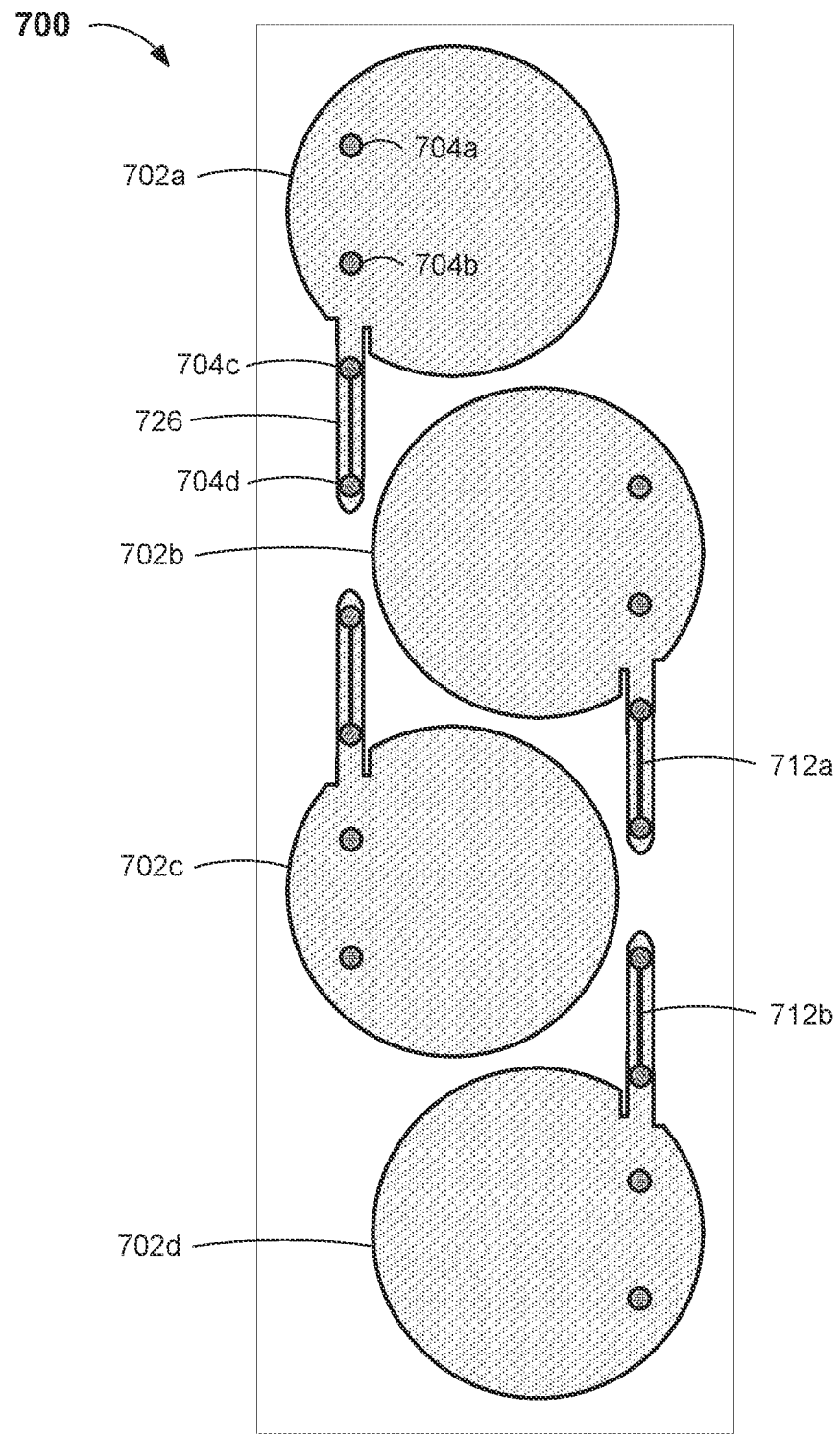
FIG. 7 illustrates a plan view of a flexible PCB material configured to fabricate flexible PCBs each having a foldable arm according to embodiments.

FIG. 7 illustrates a flexible PCB material 700 configured to optimize an automated fabrication of a flexible PCB having a foldable arm, such as, e.g., flexible PCB 602, in accordance with one or more embodiments. As shown, flexible PCB material 700 may be configured to have a closely arranged grouping of flexible PCBs 702a-702d to minimize unused PCB material. Each flexible PCB 702a-702d may have four battery contact pads 704a-704d (only one group of battery contact pads is labeled in FIG. 7) to accommodate two coin cell (or similarly configured) batteries. Other embodiments configured for a single battery may only have two battery contact pads, such as, e.g., battery contact pad 704a and 704d. Each of battery contact pads 704a-704d may be similar or identical to battery contact pad 104. Each flexible PCB 702a-702d may also have a foldable arm 726 (only one labeled), which may be similar or identical to foldable arm 626. Each flexible PCB 702a-702d may further have printed conductors 712a and 712b (only one each labeled), wherein printed conductor 712a is formed on one surface of foldable arm 726 to connect battery contact pads 704c and 704d to each other, and a printed conductor 712b is formed on an opposite surface of foldable arm 726 to also connect battery contact pads 704c and 704d to each other. Although a single column of four flexible PCBs 702a-702d is shown in FIG. 7, other embodiments of PCB material may have other numbers of columns and/or closely arranged groupings of flexible PCBs based on the configuration shown.

Figure 8:
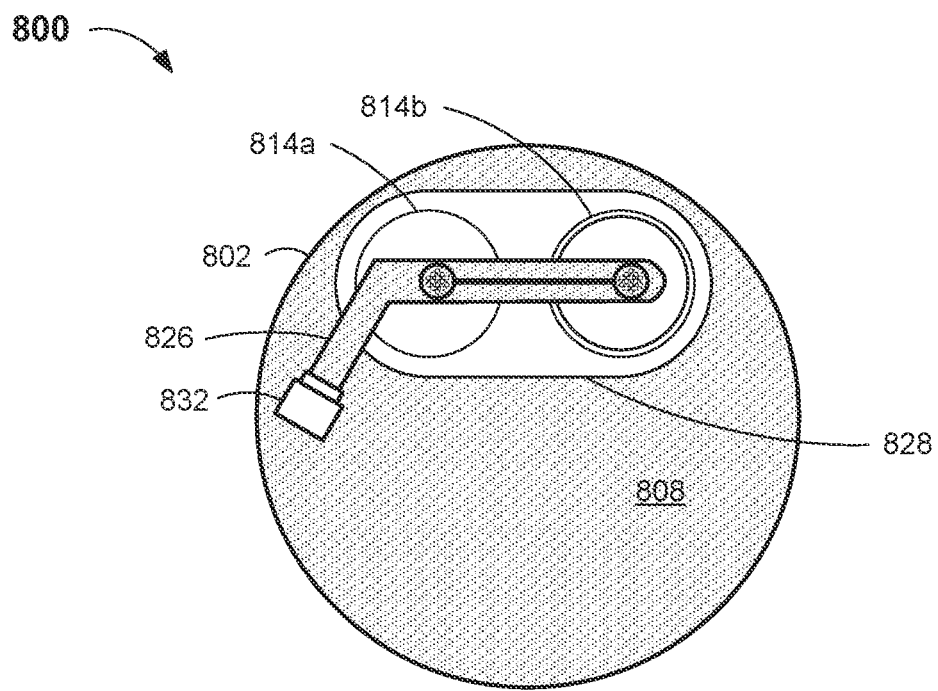
FIG. 8 illustrates a plan view of a flexible PCB having an attachable arm to mount and electrically connect a pair of coin cell batteries to the flexible PCB according to embodiments.

FIG. 8 illustrates a flexible PCB configuration 800 having an attachable arm 826 configured to mount and electrically connect a pair of coin cell batteries 814a and 814b (or batteries with a similar configuration) to a flexible PCB 802 in accordance with one or more embodiments. Batteries 814a and 814b may be placed on a top surface 808 of flexible PCB 802 over respective battery contact pads (not shown) formed in flexible PCB 802. Each of the battery contact pads formed in flexible PCB 802 may be similar or identical to battery contact pad 104 of FIGS. 1A and 1B. In those embodiments where some rigidity to the area where the battery or batteries are to be mounted is desired to facilitate an assembly process of flexible PCB 802, a non-conductive battery stiffener 828 may be used to hold batteries 814a and 814b. Battery stiffener 828 may be identical or similar to battery stiffener 626 of FIG. 6.

Figure 9:
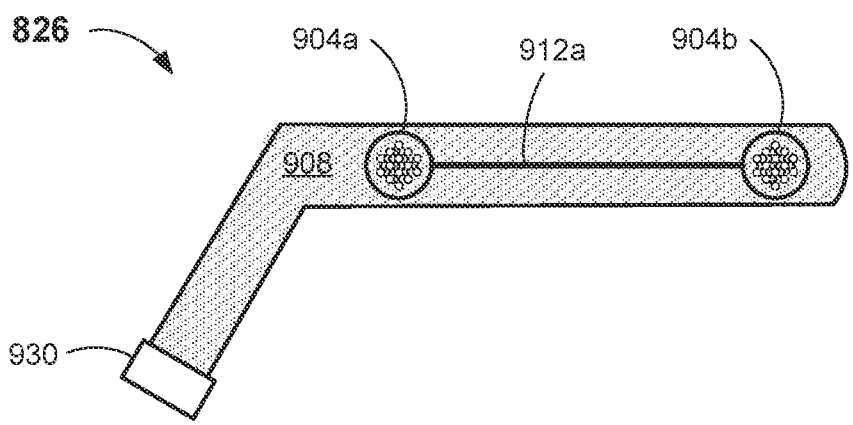
FIG. 9 illustrates a plan view of the attachable arm of FIG. 8 according to embodiments.

As shown in FIG. 9, attachable arm 826 is a separate part that may have battery contact pads 904a and 904b formed therein that may be connected to each other by a printed conductor 912a on one surface of attachable arm 826 and, in some embodiments, by a printed conductor (not shown) on the opposite surface of attachable arm 826. Each of battery contact pads 904a and 904b may be similar or identical to battery contact pad 104. Attachable arm 826 may also have a single-ended termination 930 formed at one end of attachable arm 826 that is configured to be inserted into a connector 832 mounted on top surface 808 of flexible PCB 802. In the two-battery embodiment shown in FIG. 8, the connection of single-ended termination 930 to connector 832 may be just a physical connection (no electrical connection at connector 832). In other embodiments using only a single battery, the connection of single-ended termination 930 to connector 832 may be a physical and electrical connection (to complete the circuit with the single battery) wherein attachable arm 826 may include a printed conductor extending from the battery contact pad to the single-ended termination 930 for an electrical connection from the top surface terminal of the battery through connector 832 to circuitry imprinted on top surface 808. In some embodiments, connector 832 may be an FPC (flexible printed circuit) connector. Other suitable connectors may be used. The shape of attachable arm 826 and the placement of connector 832 on top surface 808 are configured such that attachable arm 826 when inserted in connector 832 has battery contact pad 904a positioned over and on battery 814a and battery contact pad 904b positioned over and on battery 814b. Other shapes of attachable arm 826 and placements of connector 832 are possible. In those embodiments where only a single battery is used, attachable arm 826 and flexible PCB 802 may each have just one appropriately positioned battery contact pad, and the length and/or shape of attachable arm 826 and the placement of connector 832 may be adjusted accordingly. Attachable arm 826 may be made of the same flexible PCB material as flexible PCB 802. Alternatively, other suitable materials may be used to fabricate attachable arm 826.

To complete the mechanical and electrical connections of attachable arm 826 to batteries 814a and 814b, conductive ultraviolet curable epoxy, such as, e.g., conductive ultraviolet curable epoxy 216 or 616, may be disposed over and in each of battery contact pads 904a and 904b from a top surface 908 of attachable arm 826 and cured in a same or similar manner as described above in connection with FIGS. 2, 3, 4B, 5, and 6C. Likewise, batteries 814a and 814b may be mechanically and electrically connected to top surface 808 of flexible PCB 802 by application and curing of conductive ultraviolet curable epoxy disposed over and in each of the battery contact pads formed in flexible PCB 802 from a bottom surface of flexible PCB 802 in a same or similar manner as described above in connection with FIGS. 2, 3, 4B, 5, and 6C. Note that the curing of conductive ultraviolet curable epoxies in and over battery contact pads 904a, 904b, and the two battery contact pads formed in flexible PCB 802 by ultraviolet light may be performed concurrently or in any suitable order.

Figure 10:
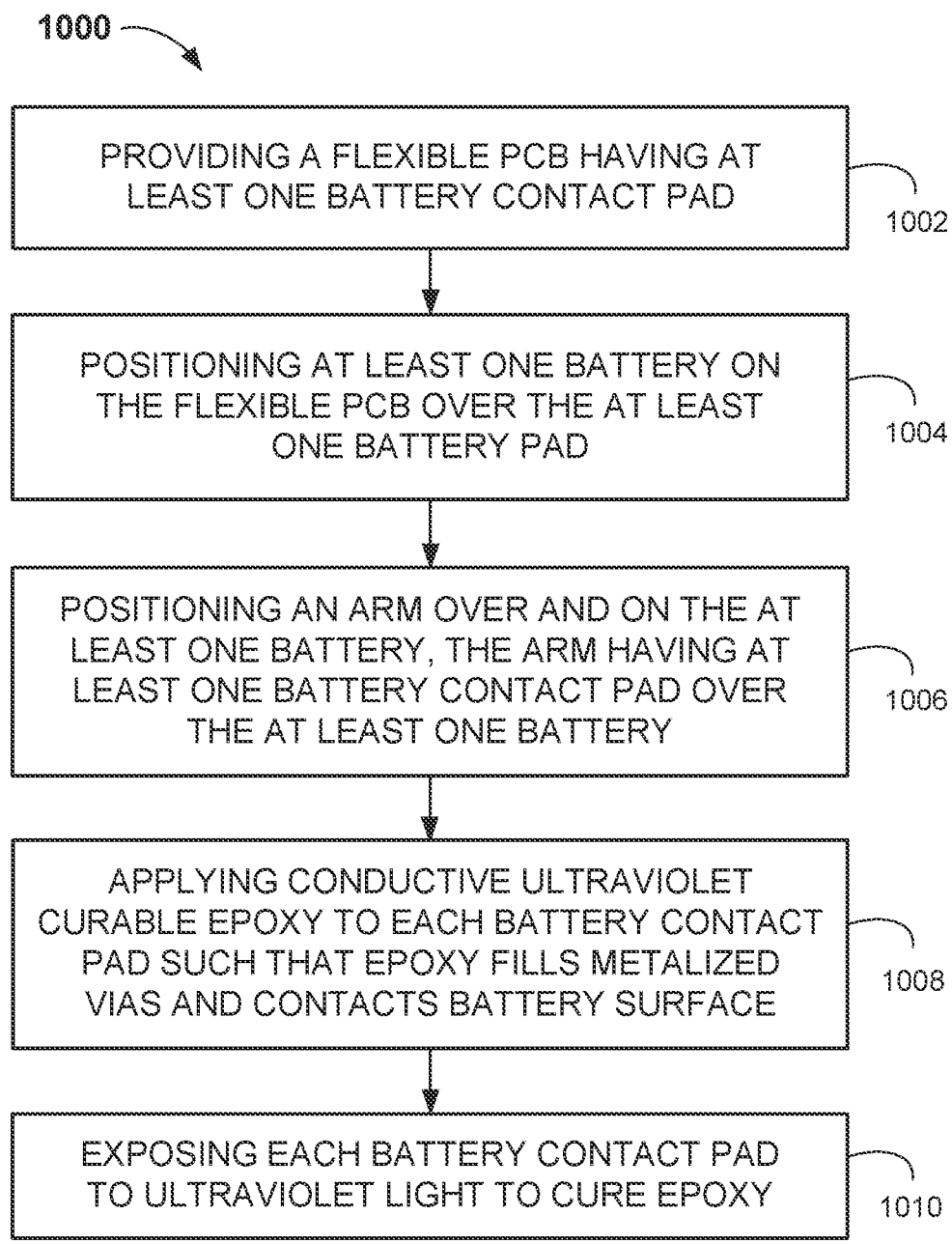
FIG. 10 illustrates a flowchart of another method of mounting a coin cell battery to a flexible PCB according to embodiments.
Figure 11:
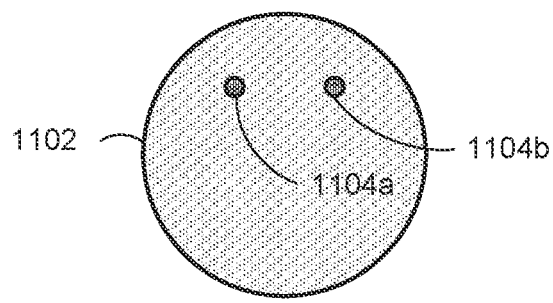
FIG. 11 illustrates a plan view of a flexible PCB having battery contact pads according to embodiments.

FIG. 10 illustrates a method 1000 of mounting a coin cell (or similarly configured) battery to a flexible PCB with an arm in accordance with one or more embodiments. At process block 1002, method 1000 can include providing a flexible PCB having at least one battery contact pad formed therein. For example, as shown in FIG. 11, flexible PCB 1102 may have one or more battery contact pads 1104a and/or 1104b formed therein. Each of battery contact pads 1104a and 1104b may be similar or identical to battery contact pad 104.

At process block 1004, method 1000 can include positioning at least one coin cell battery (or battery of similar configuration) on the flexible PCB over the at least one battery contact pad. If more than one battery is to be mounted on the flexible PCB, each battery is to be positioned over a respective battery contact pad. For example, as shown in FIGS. 6A, 6B, and 8, one or more batteries 614a, 614b, 814a, and/or 814b may be positioned on flexible PCB 602 or 802 over a respective battery contact pad. If two batteries (e.g., batteries 614a and 614b or batteries 814a and 814b) are to be positioned, battery stiffener 628 or 828 may be used, if desired, to add rigidity to the battery mounting area of the flexible PCB.

At process block 1006, method 1000 can include positioning an arm over and on the at least one battery, the arm having at least one battery contact pad formed therein and positioned over and on the at least one battery. If more than one battery is to be mounted on the flexible PCB, the arm has a respective battery contact pad formed therein for each battery. The battery contact pads are appropriately spaced apart from each other on the arm to accommodate positioning over respective batteries under the arm. One or more printed conductors formed on the arm may electrically connect the battery contact pads to each other. Referring to FIGS. 6A-6C, 8, and 9, the arm may be, e.g., foldable arm 626 or attachable arm 826. In those embodiments where the arm is foldable arm 626, method 1000 at process block 1006 includes folding the arm such that foldable arm 626 is positioned over and on the at least one battery and the one or more battery contact pads of foldable arm 626 are positioned over and on the one or more batteries, respectively, as shown in FIGS. 6B and 6C. In those embodiments where the arm is attachable arm 826, method 1000 at process block 1006 includes inserting the single-ended termination 930 of attachable arm 826 in connector 832 such that attachable arm 826 is positioned over and on the at least one battery and the one or more battery contact pads of attachable arm 826 are positioned over and on the one or more batteries, respectively, as shown in FIG. 8.

At process block 1008, method 1000 can include applying conductive ultraviolet curable epoxy to the accessible side of each contact pad such that the epoxy fills the metalized vias of each contact pad and contacts the battery surface, as similarly described above in connection with process block 506 of method 500 (FIG. 5).

And at process block 1010, method 1000 can include exposing each battery contact pad to ultraviolet light to cure the conductive ultraviolet curable epoxy, as similarly described above in connection with process block 508 of method 500 (FIG. 5). Mechanical and electrical connections between the battery and the battery contact pads formed in the arm and flexible PCB are thus established.

Figure 12:
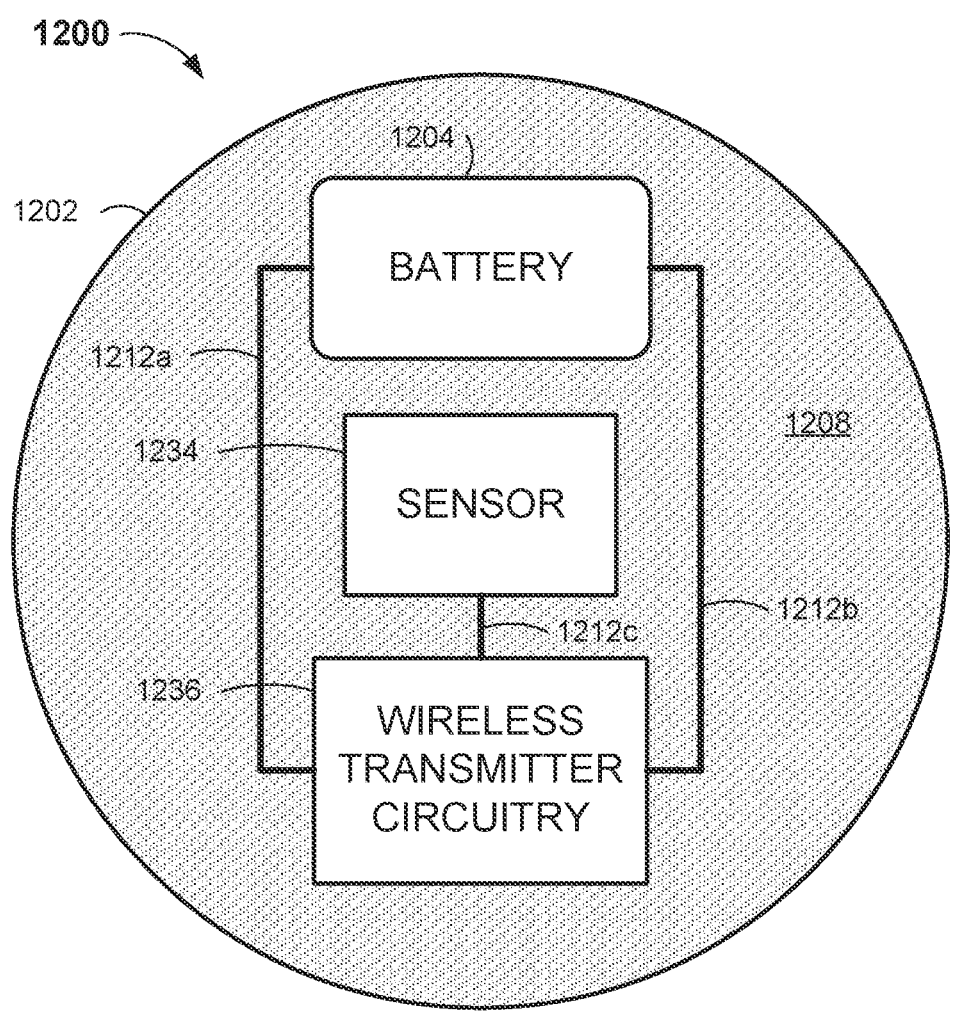
FIG. 12 illustrates a simplified plan view block diagram of a continuous glucose monitor (CGM) wireless transmitter having a flexible PCB according to embodiments.

FIG. 12 illustrates a continuous glucose monitor (CGM) wireless transmitter 1200 having a flexible PCB in accordance with one or more embodiments. CGM wireless transmitter 1200 includes a flexible PCB 1202 having one or more batteries 1204 mounted thereon. One or more batteries 1204 may be mounted on and electrically connected to flexible PCB 1202 in any manner shown in FIGS. 2, 4B, 6B, 6C, and/or 8. CGM wireless transmitter 1200 also includes a glucose sensor 1234 and wireless transmitter circuitry 1236 each fabricated on top surface 1208 (or alternatively on a bottom surface) of flexible PCB 1202 and electrically connected to each other, to one or more batteries 1204, and to possibly other circuits or components (not shown) by printed conductors 1212a, 1212b, and 1212c. A portion of glucose sensor 1234 is inserted into the skin of a user's body and may be configured to continually measure glucose levels, and wireless transmitter circuitry 1236 may be configured to wirelessly transmit those glucose measurements to a CGM receiver and/or insulin pump. Other circuits and circuit components (not shown) may also be fabricated on flexible PCB 1202. Advantageously, CGM wireless transmitter 1200 is capable of bending and/or flexing such that it may conform to a surface of the user's body to which it is attached, improving the adherence of CGM wireless transmitter 1200 to the skin surface and/or the user's comfort while wearing CGM wireless transmitter 1200.

In some embodiments, other light curable epoxies may be employed, such as epoxies that are curable at other wavelengths (e.g., wavelengths for middle-ultraviolet light, near-ultraviolet light, violet light, blue light, etc., or other visible wavelengths). For example, in some embodiments, methods 300, 500, 1000, may be employed with other light curable epoxies, as may any of the circuit board configurations described herein.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure but, to the contrary, to cover all modifications, equivalents, and alternatives falling within the scope of the claims.

What is claimed is:

1. A flexible printed circuit board (PCB), comprising:
a metalized via extending through the flexible PCB from a first surface to an opposite second surface of the flexible PCB;
a battery in contact with the second surface and covering the metalized via; and
a conductive light curable epoxy disposed on the first surface over and in the metalized via such that the conductive light curable epoxy contacts and adheres to the battery and provides a conductive path from the battery to the metalized via.

2. The flexible PCB of claim 1, further comprising a printed conductor surrounding the metalized via on the first surface such that the conductive path extends from the battery to the printed conductor.

3. The flexible PCB of claim 1, further comprising a contact pad, wherein the contact pad comprises the metalized via and a plurality of other metalized vias arranged in a pattern, a printed conductor surrounding and electrically connecting each of the metalized vias in the pattern.

4. The flexible PCB of claim 3, wherein the conductive light curable epoxy is disposed on the contact pad on the first surface over and in each of the metalized vias in the pattern such that the conductive light curable epoxy contacts and adheres to the battery and provides a conductive path from the battery to the printed conductor.

5. The flexible PCB of claim 1, wherein the battery is a coin cell battery.

6. The flexible PCB of claim 1, further comprising wireless transmitter circuitry fabricated on the first surface of the flexible PCB.

7. A continuous glucose monitor, comprising:
the flexible PCB of claim 6; and
a sensor coupled to the wireless transmitter circuitry, the sensor configured to measure a glucose level.

8. A flexible printed circuit board (PCB), comprising:
first and second sections, the first section separated from the second section by a slit extending through the flexible PCB from a top surface to a bottom surface;
a first metalized via extending through the flexible PCB from the top surface to the bottom surface in the first section;
a second metalized via extending through the flexible PCB from the top surface to the bottom surface in the second section;
a battery inserted in the slit such that the battery contacts the bottom surface of the first section under the first metalized via and contacts the top surface of the second section over the second metalized via;
a first conductive light curable epoxy disposed on the top surface of the first section over and in the first metalized via such that the first conductive light curable epoxy contacts and adheres to the battery and provides a conductive path from the battery to the first metalized via; and
a second conductive light curable epoxy disposed on the bottom surface of the second section over and in the second metalized via such that the second conductive light curable epoxy contacts and adheres to the battery and provides a conductive path from the battery to the second metalized via.

9. The flexible PCB of claim 8, further comprising a first contact pad in the first section, wherein the first contact pad comprises the first metalized via and a first plurality of other metalized vias arranged in a first pattern, a first printed conductor surrounding and electrically connecting each of the metalized vias in the first pattern.

10. The flexible PCB of claim 9, further comprising a second contact pad in the second section, wherein the second contact pad comprises the second metalized via and a second plurality of other metalized vias arranged in a second pattern, a second printed conductor surrounding and electrically connecting each of the metalized vias in the second pattern.

11. The flexible PCB of claim 8, further comprising wireless transmitter circuitry fabricated on the first surface of the flexible PCB.

12. A continuous glucose monitor, comprising:
the flexible PCB of claim 11; and
a sensor coupled to the wireless transmitter circuitry, the sensor configured to measure a glucose level.

13. A flexible printed circuit board (PCB), comprising:
a first metalized via extending through the flexible PCB from a top surface to a bottom surface of the flexible PCB;
a battery positioned on the top surface over the first metalized via;
a first conductive light curable epoxy disposed on the bottom surface of the flexible PCB over and in the first metalized via such that the first conductive light curable epoxy contacts and adheres to the battery and provides a conductive path from the battery to the first metalized via;
an arm having a second metalized via extending through the arm from a top surface to a bottom surface of the arm, the arm positioned on the battery such that the bottom surface of the arm contacts the battery and the second metalized via is over the battery; and a second conductive light curable epoxy disposed on the top surface of the arm over and in the second metalized via such that the second conductive light curable epoxy contacts and adheres to the battery and provides a conductive path from the battery to the second metalized via.

14. The flexible PCB of claim 13, wherein the arm initially extends outward from the flexible PCB and is foldable onto the battery.

15. The flexible PCB of claim 13, further comprising a connector on the top surface of the flexible PCB, wherein the arm has an end inserted in the connector.

16. The flexible PCB of claim 15, wherein the connector is a flexible printed circuit (FPC) connector.

17. The flexible PCB of claim 13, further comprising a non-conductive stiffener sized to hold the battery, the non-conductive stiffener having a thickness or height no greater than a thickness or height of the battery.

18. The flexible PCB of claim 13, further comprising a first contact pad that includes the first metalized via and a first plurality of other metalized vias arranged in a first pattern, a first printed conductor surrounding and electrically connecting each of the metalized vias in the first pattern.

19. The flexible PCB of claim 13, wherein the arm comprises a second contact pad that includes the second metalized via and a second plurality of other metalized vias arranged in a second pattern, a second printed conductor surrounding and electrically connecting each of the metalized vias in the second pattern.

20. A continuous glucose monitor, comprising:
the flexible PCB of claim 13 further comprising wireless transmitter circuitry fabricated on the top surface of the flexible PCB; and
a sensor coupled to the wireless transmitter circuitry, the sensor configured to measure a glucose level.

* * * * *